United States Patent [19]
Elghazzawi

[11] Patent Number: 5,685,318
[45] Date of Patent: Nov. 11, 1997

[54] METHOD AND APPARATUS FOR DETECTING QUICK MOVEMENT ARTIFACT IN IMPEDANCE RESPIRATION SIGNALS

[75] Inventor: Ziad F. Elghazzawi, Medford, Mass.

[73] Assignee: Siemens Medical Systems, Inc., Iselin, N.J.

[21] Appl. No.: 536,018

[22] Filed: Sep. 29, 1995

[51] Int. Cl.⁶ ................................................. A61B 5/008
[52] U.S. Cl. ................................................. 128/716
[58] Field of Search ................... 128/716, 718–724

[56] References Cited

U.S. PATENT DOCUMENTS

| | | | |
|---|---|---|---|
| 3,911,899 | 10/1975 | Hattes | 128/721 |
| 4,197,856 | 4/1980 | Northrop | 128/721 |
| 4,289,142 | 9/1981 | Kearns | 128/723 |
| 4,365,636 | 12/1982 | Barker | 128/716 |

*Primary Examiner*—Jennifer Bahr
*Assistant Examiner*—Bryan K. Yarnell
*Attorney, Agent, or Firm*—Lawrence C. Edelman

[57] ABSTRACT

An apparatus for monitoring the respirations of a patient includes a device for generating a respiration signal having amplitude modulations representative of patient respirations, as well as respiration artifacts, and a processor coupled to the respiration signal generating device and responsive to the respiration signal for 1) detecting inflection points in the respiration signal; 2) determining if either one of a portion of the respiration signal which precedes or follows each detected inflection point has a slope which exceeds a predetermined slope threshold level which is indicative of a respiration artifact; and 3) developing breath indication information based upon the slope threshold determination.

4 Claims, 3 Drawing Sheets

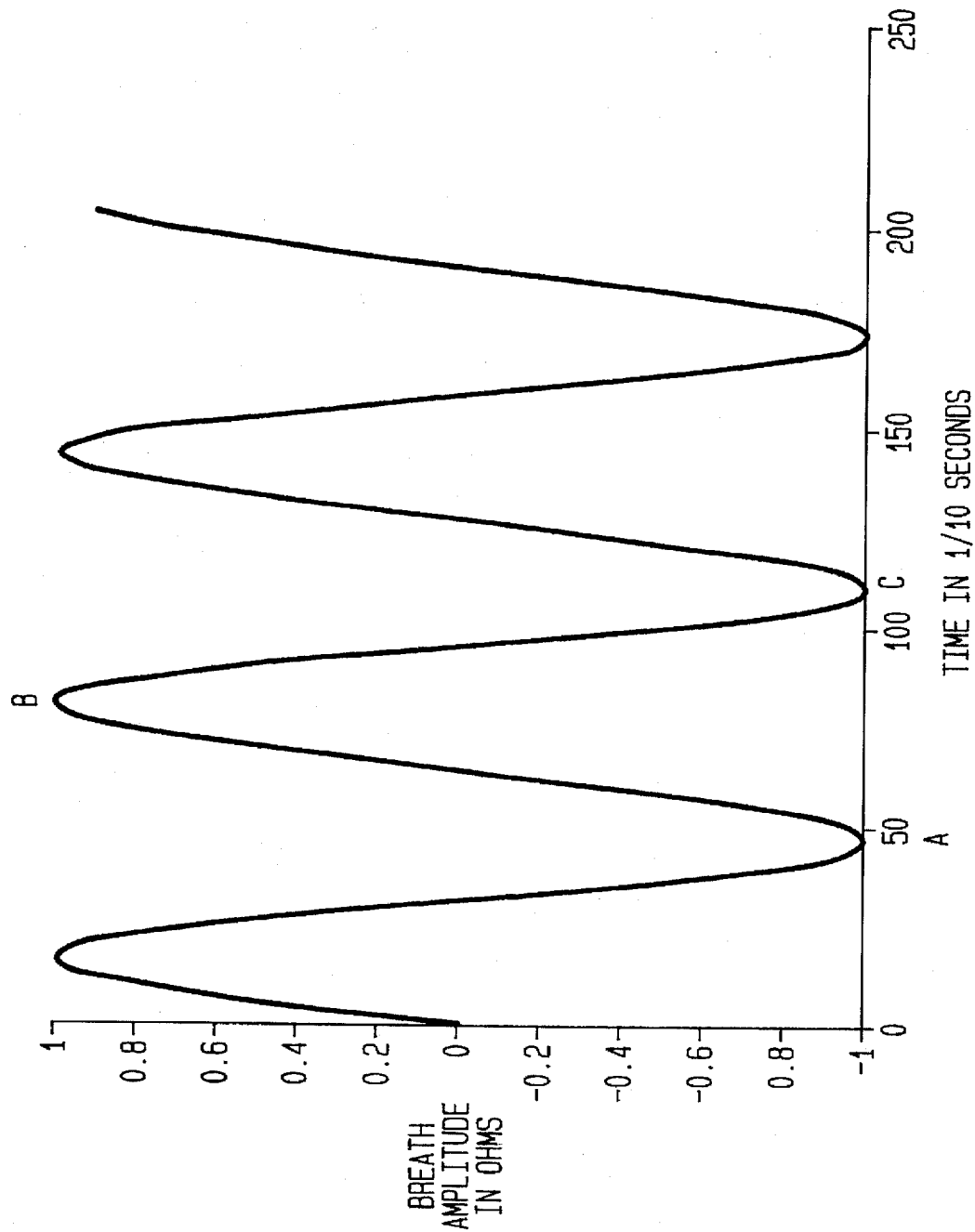

METHOD AND APPARATUS FOR DETECTING QUICK MOVEMENT ARTIFACT IN IMPEDANCE RESPIRATION SIGNALS

BACKGROUND OF THE INVENTION

1. Field of the Invention

The present invention relates to a method and apparatus for improving the accuracy of a respiration monitor, and more specifically, to preventing quick movement related artifacts from being counted as breaths, and thereby preventing false alarms (such as high respiration rate) from being generated.

2. Description of Prior Art

Typically, a differential, constant amplitude AC examination current is applied to the body of a patient for detecting patient respirations by measuring changes in the transthoracic impedance of the patient. As shown in FIG. 1, the examination current is applied to a patient 10 by two (i.e., 12 and 14) of the plural electrodes normally used for ECG monitoring and mounted on the patient 10. The examination current is passed through the thoracic cavity of the patient and, due to the constant amplitude examination current passing through a transthoracic impedance that changes with patient respirations, voltage modulations are created between ECG electrodes 10 and 12 in accordance with the patient respirations. The EKG electrodes are connected to a patient bedside monitor 18 via leads in an ECG cable 16. The resulting voltage modulations are typically detected in the bedside monitor by a synchronous voltage detector, connected to the same pair of electrodes as was used for applying the examination current, such as the right arm (RA) and left arm (LA) electrodes. In a manner well known to those of ordinary skill in the art, these sensed voltage amplitude modulations are processed for developing a respiration signal which may be used for display and/or alarm monitoring of the respirations of the patient.

Unfortunately, one problem in the prior art apparatus is inaccuracies in developing respiration rate and alarm information from the sensed voltage amplitude modulations, due to movement related voltage amplitude modulations (i.e., artifacts).

It would be desirable to simply and accurately reduce, and preferably eliminate these artifacts.

SUMMARY OF THE INVENTION

An apparatus for monitoring the respirations of a patient comprises, generating means for generating a respiration signal having amplitude modulations representative of patient respirations, as well as respiration artifacts, and processing means coupled to the generating means and responsive to the respiration signal for:

1) detecting inflection points in the respiration signal;
2) determining if the slope of either one of a portion of the respiration signal which precedes or follows each detected inflection point exceeds a predetermined threshold level; and
3) developing breath indication information based upon the slope threshold determination.

BRIEF DESCRIPTION OF THE DRAWINGS

FIG. 4 illustrates a respiration signal waveform, useful for understanding the respiration processing shown in FIG. 3.

DETAILED DESCRIPTION OF THE INVENTION

Figure 1:
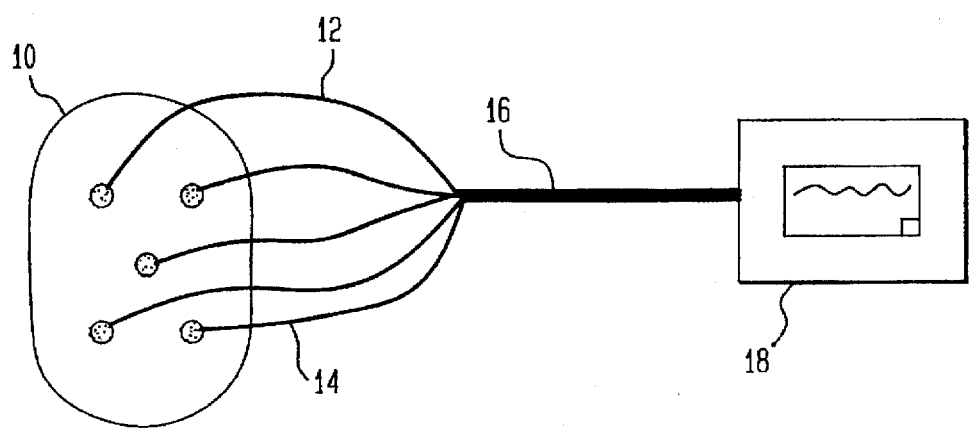
FIG. 1 illustrates in block diagram form a patient respiration monitoring system.
Figure 2:
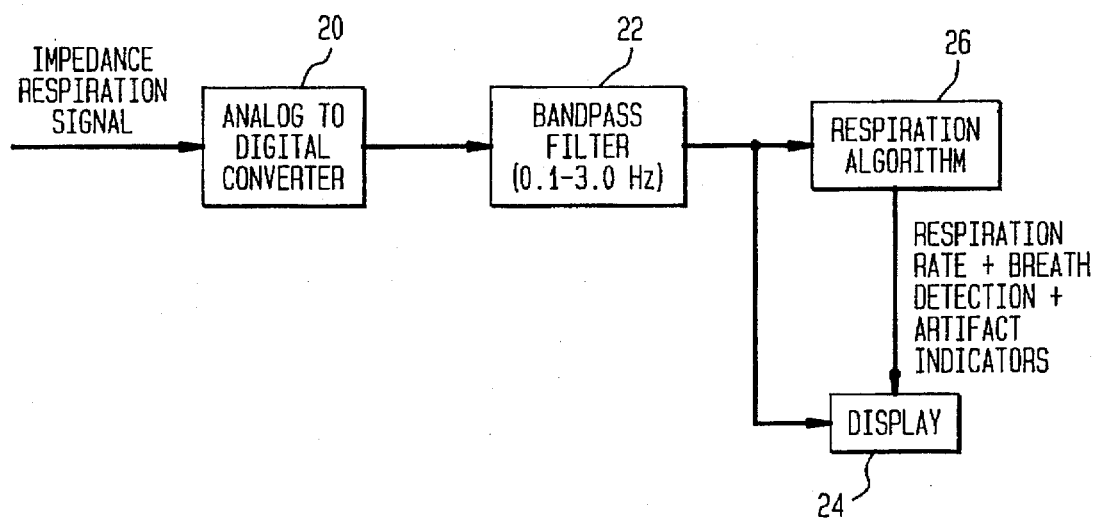
FIG. 2 illustrates in block diagram form a more detailed portion of the patient respiration monitoring system shown in FIG. 1.

As shown and previously described in conjunction with FIG. 1, the patient respiration monitor 18 includes respiration circuitry, such as a synchronous detector (not specifically shown) for initially developing an impedance respiration signal. As shown in FIG. 2 the impedance respiration signal is then digitized by a digital to analog converter stage 20. After application to a bandpass filter 22 where it is bandpass filtered (typically 0.1 to 3.0 Hz) it is applied to a display 24 for displaying a respiration waveform. Monitor 18 includes a processor portion 26 for further processing of the respiration signal for developing respiration rate information, as well as respiration alarms.

In accordance with the principles of the invention, the respiration signal processing by processor. 26 is improved over the prior art signal processing so as to more accurately detect signal artifacts and result in developing and displaying more accurate respiration information. As shown in FIG. 2, the processor 26 provides to display 24 respiration rate data, as well as breath indications, such as a flashing "lung" icon, and provides real time respiration artifact information to the user.

Figure 3:
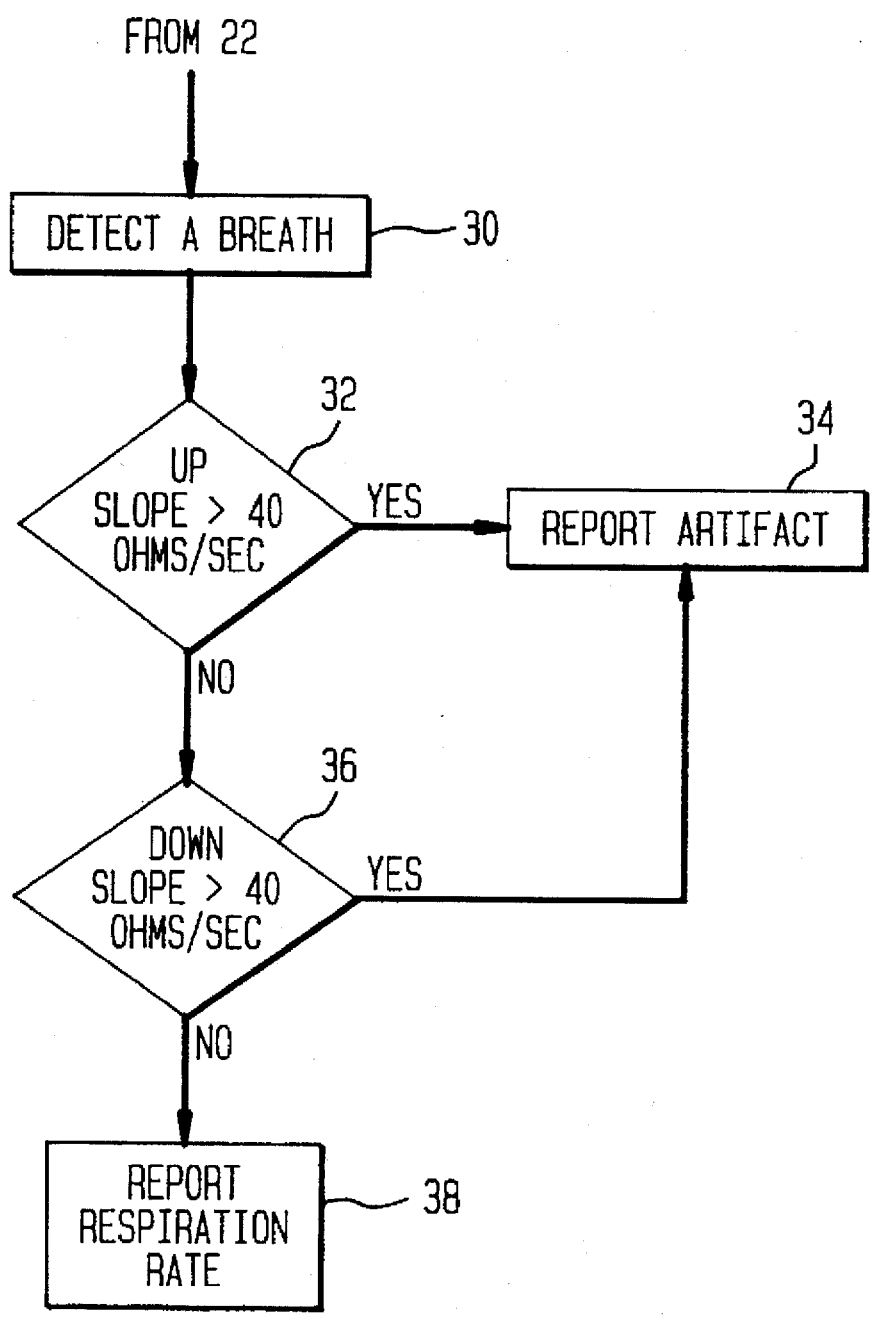
FIG. 3 illustrates in flow diagram form a portion of the respiration processing shown in FIG. 2.

The inventive respiration signal processing will next be described in conjunction with FIG. 3. A breath detect step 30 is responsive to the signal at the output of filter 22 for detecting breaths based on sensing an up rise followed by a down rise after exceeding a certain detection threshold in both directions (i.e., an inflection). Such inflections of the respiration signal are shown, for example by points A, B and C in the respiration signal waveform shown in FIG. 4. The up-rise (from point A to point B in FIG. 4) represents the inspiration of air by the patient, and the down-rise (from point B to point C) represents the expiration of air by the patient. The detection threshold can be set automatically by the respiration signal processing ((B−A)/3) or set by the user by adjusting the threshold while watching the display of the respiration information on the monitor display 24. Typically, this threshold is set to a point between 0.15 Ohms to 2.0 Ohms.

The new method for detecting artifacts detects quick movement artifacts by checking for both the down rise and up rise slopes of the respiration signal. If any of these slopes exceeds a certain predetermined threshold (i.e., in the illustrated embodiment 40 Ohms/sec), this breath is rejected and is considered an artifact.

As shown by step 32, the maximum slope between point A and point B in FIG. 4 is determined. If this slope exceeds the limit (40 Ohms/sec), the breath corresponding to this up slope is rejected, considered artifact, and reported to display 24 via artifact report step 34. Also, in step 36 the maximum slope between point B and point C on the same breath deflection is determined. If this slope exceeds the limit (40 Ohm/sec), the breath corresponding to this up slope is rejected, considered artifact, and reported to display 24 via artifact report step 34.

As shown by step 38, if neither slope exceeds the maximum slope limits, an indication is provided to display 24, which in the illustrated embodiment comprises illuminating an icon (lung) on a portion of display 24. A portion for display of the processed respiration information is illustrated in the lower right portion of the display shown in FIG. 1 on monitor 18. A respiration waveform is shown displayed on another portion of the display shown in FIG. 1 on monitor 18.

The rational behind limiting the slope to a certain threshold is that human airways and lungs have a certain capacity in volume and speed in moving air in and out. This in and out movement of air represents breaths which are represented as deflections on the impedance respiration signal. The limited capacity in volume and speed in moving air in and out of the human airway and lungs is reflected on the impedance respiration signal as a limitation on the steepness of the up and down slew rate of the signal which represents a breath. From a study on neonatal, pediatric and adult respiration waveform data the present inventor has found that the limit on up and down slope on the respiration waveform during a breath would not exceed 40 Ohms/sec.

Thus, there has been shown and described a novel method and apparatus which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, the maximum slope threshold of 40 Ohms/sec. in the illustrated embodiment could be changed to a different value, for example when monitoring neonates, as compared to monitoring adults. Additionally, the threshold value can be made adaptive. Furthermore, although in the preferred embodiment both the up-slope and down-slope are compared to a slope threshold, in an alternative embodiment only one of these slopes may be monitored for breath qualification. Finally, although in the preferred embodiment the respiration signal is generated using an impedance pneumography, by measuring the change in the transthoracic impedance of the patient, in an alternative embodiment the respiration signal may be generated using by more directly monitoring the exhaled air of the patient. All such changes, modifications, variations and other uses and applications which do not depart from the spirit and scope of the invention are deemed to be covered by the invention which is limited only by the claims which follow.

We claim:

1. An apparatus for monitoring the respirations of a patient, comprising:

generating means for generating a respiration signal having amplitude modulations representative of patient respirations, as well as respiration artifacts; and processing means coupled to said generating means and responsive to said respiration signal for:

1) detecting inflection points in said respiration signal;
2) determining if either one of a portion of said respiration signal which precedes or follows each detected inflection point has a slope which exceeds a predetermined slope threshold level which is indicative of a respiration artifact; and
3) only developing breath indication information when said slope threshold determination determines that neither one of said preceding or following portions of said respiration signal exceeded said predetermined slope threshold.

2. The apparatus of claim 1, further including a display, responsive to said respiration signal for displaying said respiration signal.

3. The apparatus of claim 2, wherein said display includes a first portion for displaying said respiration signal, and a second portion for displaying said breath information developed by said processing means.

4. A method for monitoring the respirations of a patient, comprising:

generating a respiration signal having amplitude modulations representative of patient respirations, as well as respiration artifacts; and processing means coupled to said generating means and responsive to said respiration signal for:

1) detecting inflection points in said respiration signal;
2) determining if either one of a portion of said respiration signal which precedes or follows each detected inflection point has a slope which exceeds a predetermined slope threshold level which is indicative of a respiration artifact; and
3) only developing breath indication information when said slope threshold determination determines that neither one of said preceding or following portions of said respiration signal exceeded said predetermined slope threshold.

* * * * *